(12) United States Patent
Shen

(10) Patent No.: US 7,122,353 B2
(45) Date of Patent: Oct. 17, 2006

(54) TARGETED CARRIER FUSIONS FOR DELIVERY OF CHEMOTHERAPEUTIC AGENTS

(75) Inventor: Ben Shen, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/912,764

(22) Filed: Aug. 5, 2004

(65) Prior Publication Data

US 2005/0059122 A1 Mar. 17, 2005

Related U.S. Application Data

(60) Provisional application No. 60/492,508, filed on Aug. 5, 2003.

(51) Int. Cl.
*C12P 19/00* (2006.01)

(52) U.S. Cl. .................................................... 435/69.7

(58) Field of Classification Search ................ 530/350; 514/12; 435/69.1, 69.7
See application file for complete search history.

(56) References Cited

U.S. PATENT DOCUMENTS

2002/0182671 A1* 12/2002 Lal et al. .................... 435/69.1
2005/0042753 A1* 2/2005 Yang et al. .................. 435/455

FOREIGN PATENT DOCUMENTS

| WO | WO 87/02061 | * 4/1987 |
| WO | WO 95/03064 | 2/1995 |
| WO | WO 98/10795 | 3/1998 |
| WO | WO 01/53342 | 7/2001 |

OTHER PUBLICATIONS

Aina et al., "Therapeutic cancer targeting peptides," *Pept. Sci.*, 66:184-199, 2002.
Martin et al., "Molecular basis of mitomycin C resistance in Streptomyces: structure and function of the MRD protein," *Structure*, 10:933-942, 2002.
Shen et al., "Enediyne natural products: biosynthesis and prospect towards engineering novel antitumor agents," *Current Medicinal Chemistry*, 10(1):1241-1253, 2003.
Sugiyama et al., "The 1.6-Å crystal structure of the copper(II)-bound bleomycin complexed with the bleomycin-binding protein from bleomycin-producing streptomyces verticillus," *J. Biol. Chem.*, 277(3):2311-2320, 2002.
Tanaka et al., "Solution structures of C-1027 apoprotein and its complex with the aromatized chromophore," *J. Mol. Biol.*, 309:267-283, 2001.
Thornson et al., "Enediyne biosynthesis and self-resistance: a progress report," *Bioorganic Chemistry*, 27(2):172-188, 1999.
Sheldon et al., "Characterization of a mitomycin-binding drug resistance mechanism from the producing organism, *streptomyces lavendulae*," *J. Bacter.*, 179(5):1796-1804, 1997.

* cited by examiner

*Primary Examiner*—Karen Cochrane Carlson
*Assistant Examiner*—Agnes B. Rooke
(74) *Attorney, Agent, or Firm*—Fulbright & Jaworski

(57) ABSTRACT

The present invention provides for fusion proteins that act as targeted drug carries. The proteins are derived from molecules that possess natural drug-binding capabilities that are further engineered to target specific cell types, and optionally to have altered/improved drug binding characteristics. These fusion proteins are useful in, for example, delivery of chemotherapeutic compounds to cancer cells.

14 Claims, 6 Drawing Sheets

$$
\text{CNGRC} = \begin{bmatrix} \underline{\text{HindIII}} & & & & & \underline{\text{EcoRI}} \\ \text{5'-AGCTTGGTGGC TGT AAC GGC CGC TGC GGTGGCGAATTCA-3'} \\ \text{3'-ACCACCG ACA TTG CCG GCG ACG CCACCGCTTAAGTGATC-5'} \\ & & & & & \overline{\text{SpeI}} \end{bmatrix}
$$

$$
\text{CDCRGDCFC} = \begin{bmatrix} \underline{\text{HindIII}} & & & & & & & & \underline{\text{EcoRI}} \\ \text{5'-AGCTTGGTGGC TGC GAC TGT CGC GGC GAT TGC TTC TGT GGTGGCGAATTCA-3'} \\ \text{3'-ACCACCG ACG CTG ACA GCG CCG CTA ACG AAG ACA CCACCGCTTAAGTGATC-5'} \\ & & & & & & & & \overline{\text{SpeI}} \end{bmatrix}
$$

$$
\text{SMSIARL} = \begin{bmatrix} \underline{\text{HindIII}} & & & & & & \underline{\text{EcoRI}} \\ \text{5'-AGCTTGGTGGC AGC ATG AGC ATC GCG CGC CTG GGTGGCGAATTCA-3'} \\ \text{3'-ACCACCG TCG TAC TCG TAG CGC GCG GAC CCACCGCTTAAGTGATC-5'} \\ & & & & & & \overline{\text{SpeI}} \end{bmatrix}
$$

FIG. 2A pET14M/CTP
- His$_6$ - NdeI-ClaI-HindIII - NGR - EcoRI-SpeI-XhoI
- His$_6$ - NdeI-ClaI-HindIII - RGD - EcoRI-SpeI-XhoI
- His$_6$ - NdeI-ClaI-HindIII - SMS - EcoRI-SpeI-XhoI pET37M/CTP
- NdeI-ClaI-HindIII - NGR - EcoRI-SpeI-XhoI - His$_8$
- NdeI-ClaI-HindIII - RGD - EcoRI-SpeI-XhoI - His$_8$
- NdeI-ClaI-HindIII - SMS - EcoRI-SpeI-XhoI - His$_8$

FIG. 2B

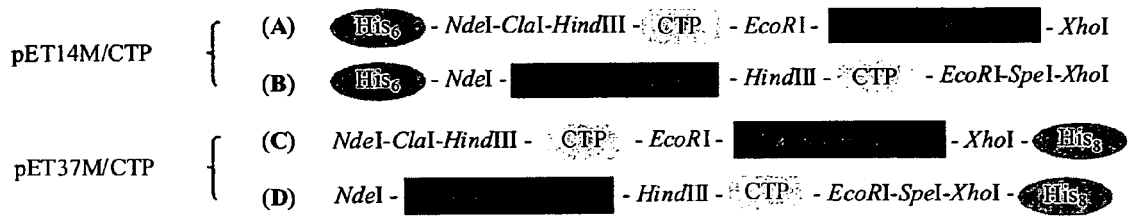
FIG. 3 A-D

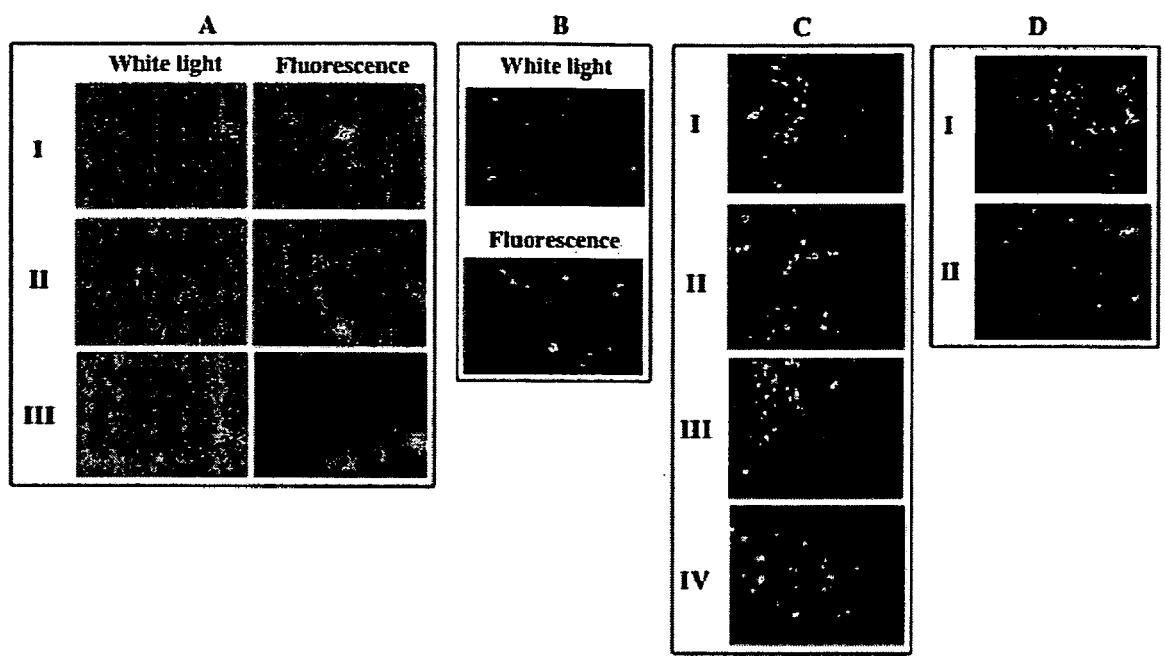
FIG. 6A-D

```
                        SEQUENCE LISTING

<160> NUMBER OF SEQ ID NOS: 63

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Lys Asn Gly Pro Trp Tyr Ala Tyr Thr Gly Arg Gln
 1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (6)
<223> OTHER INFORMATION: X = anything

<400> SEQUENCE: 2

Asn Trp Ala Val Trp Xaa Lys Arg
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (2)..(3)
<223> OTHER INFORMATION: X = anything

<400> SEQUENCE: 3

Tyr Xaa Xaa Glu Asp Leu Arg Arg Arg
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(2)
<223> OTHER INFORMATION: X = anything
```

```
<400> SEQUENCE: 4

Xaa Xaa Pro Val Asp His Gly Leu
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Leu Val Arg Ser Thr Gly Gln Phe Val
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Leu Val Ser Pro Ser Gly Ser Trp Thr
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Ala Leu Arg Pro Ser Gly Glu Trp Leu
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Ala Ile Met Ala Ser Gly Gln Trp Leu
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Gln Ile Leu Ala Ser Gly Arg Trp Leu
  1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Arg Arg Pro Ser His Ala Met Ala Arg
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Asp Asn Asn Arg Pro Ala Asn Ser Met
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Leu Gln Asp Arg Leu Arg Phe Ala Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Pro Leu Ser Gly Asp Lys Ser Ser Thr
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Phe Asp Asp Ala Arg Leu
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 15

Phe Ser Asp Ala Arg Leu
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Phe Ser Asp Met Arg Leu
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Phe Val Asp Val Arg Leu
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Phe Thr Asp Ile Arg Leu
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Phe Asn Asp Tyr Arg Leu
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Phe Ser Asp Thr Arg Leu
 1               5
```

```
<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 21

Pro Ile His Tyr Ile Phe
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 22

Tyr Ile His Tyr Ile Phe
  1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 23

Arg Ile His Tyr Ile Phe
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 24

Ile Glu Leu Leu Gln Ala Arg
  1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (4)..(9)
<223> OTHER INFORMATION: X = anything

<400> SEQUENCE: 25

Cys Val Phe Xaa Xaa Xaa Tyr Xaa Xaa Cys
  1               5                  10

<210> SEQ ID NO 26
<211> LENGTH: 12
<212> TYPE: PRT
<213> ORGANISM: Artificial Sequence
```

```
<220> FEATURE:
<223> OTHER INFORMATION: Description of Artificial Sequence:  Synthetic
      Peptide
<220> FEATURE:
<221> NAME/KEY: MOD_RES
<222> LOCATION: (2)..(8)
<223> OTHER INFORMATION: X = anything

<400> SEQUENCE: 26

Cys Xaa Phe Xaa Xaa Xaa Tyr Xaa Tyr Leu Met Cys
 1               5                  10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (3)..(9)
<223> OTHER INFORMATION: X = anything

<400> SEQUENCE: 27

Cys Val Xaa Tyr Cys Xaa Xaa Xaa Xaa Cys Tyr Val Cys
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (3)..(12)
<223> OTHER INFORMATION: X = anything

<400> SEQUENCE: 28

Cys Val Xaa Tyr Cys Xaa Xaa Xaa Xaa Cys Trp Xaa Cys
 1               5                  10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 29

Asp Pro Arg Ala Thr Pro Gly Ser
 1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 30

His Leu Gln Leu Gln Pro Trp Tyr Pro Gln Ile Ser
 1               5                  10
```

```
<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Val Pro Trp Met Glu Pro Ala Tyr Gln Arg Phe Leu
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Thr Ser Pro Leu Asn Ile His Asn Gly Gln Lys Leu
 1               5                  10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Arg Leu Thr Gly Gly Lys Gly Val Gly
 1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Cys Asp Cys Arg Gly Asp Cys Phe Cys
 1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Ala Cys Asp Cys Arg Gly Asp Cys Gly Cys Gly
 1               5                  10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 36

Cys Asn Gly Arg Cys Val Ser Gly Cys Ala Gly Arg Cys
  1               5                  10

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Cys Asn Gly Arg Cys
  1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Cys Val Cys Asn Gly Arg Met Glu Cys
  1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Asn Gly Arg Ala His Ala
  1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Thr Ala Ala Ser Gly Val Arg Ser Met His
  1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Leu Thr Leu Arg Trp Val Gly Leu Met Ser
  1               5                  10
```

```
<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 42

Cys Gly Ser Leu Val Arg Cys
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 43

Cys Gly Leu Ser Asp Ser Cys
 1               5

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 44

Asn Arg Ser Leu Lys Arg Ile Ser Asn Lys Arg Ile Arg Arg Lys
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 45

Leu Arg Ile Lys Arg Lys Arg Arg Lys Arg Lys Lys Thr Arg Lys
 1               5                  10                  15

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 46

Asn Arg Ser Thr His Ile
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 47

Ser Met Ser Ile Ala Arg Leu
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Val Ser Phe Leu Glu Tyr Arg
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 49

Cys Pro Gly Pro Glu Gly Ala Gly Cys
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Ala Thr Trp Leu Pro Pro Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Arg Arg Lys Arg Arg Arg
1               5

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Ala Ser Ser Ser Tyr Pro Leu Ile His Trp Arg Pro Trp Ala Arg
1               5                   10                  15
```

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 53

Cys Thr Thr His Trp Gly Phe Thr Leu Cys
 1               5                  10

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
tccatatgga attcgcgccc gccttctcc                                          29

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
ttctcgagaa gctttcacgg cttggtcag                                          29

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
tccatatgga attcgcgcgc cgacggc                                            27

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
ttctcgagaa gctttcagtt gaaggagatc gc                                      32

<210> SEQ ID NO 58
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 58
gtagaattcc atatggtgaa attcttggtt gccg                          34

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59
gatctcgaga agcttctccc cgcggtgaag tg                            32

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
gtagaattcc atatggccgt attgctctcg                               30

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 61
gatctcgaga agcttacgaa ccgtccgggt cgt                           33

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62
ctagaattcc atatgtcagc aaggatttcc ctcttc                        36

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63
gatctcgaga agcttcggga ggggcgcgaa gag                           33
```

TARGETED CARRIER FUSIONS FOR DELIVERY OF CHEMOTHERAPEUTIC AGENTS

The present invention claims benefit of priority to U.S. Provisional Ser. No. 60/492,508, filed Aug. 5, 2003, the entire contents of which are hereby incorporated by reference.

The U.S. Government owns rights in the present invention pursuant to grant numbers CA78747 from the National Institutes of Health.

BACKGROUND OF THE INVENTION

1. Field of the Invention

The present invention relates to the fields of molecular biology and protein biochemistry. More specifically, the invention relates to fusion proteins that serve as targeted carriers for chemotherapeutic compounds, and methods of use therefor.

2. Related Art

Cancer continues to be one of the leading causes of death world-wide, despite impressive advances in cancer therapy in recent years. One of the most promising avenues of therapy—targeted drug deliver—has proved to be one of the biggest disappointments. Initially, much hope was focused on the use of monoclonal antibodies (mAbs), which are characterized by the high degree of binding selectivity. While preliminary worked demonstrated the feasibility of targeting tumor cell surface receptors, the actual results were less than impressive. Two major limitations inherent in the use of mAbs—their large size and non-specific uptake of antibodies by the liver and reticuloendothelial system—probably contributed significantly to the less than desired results.

Tumor targeting peptides are excellent alternative targeting agents for human cancers, and they may alleviate some of the problems with antibody targeting. In the past decade, various cancer cell surface or cancer-related targeting peptides have been identified by combinatorial methods. Conjugation of these cancer-targeting peptides to either proteins or small molecule anti-cancer drugs showed remarkable improvement in cancer cell selectivity and specificity, demonstrating that these peptides may be the second generation of targeted drug delivery for cancer. Nonetheless, improvements in the application of peptide drug targeting still are desired.

SUMMARY OF THE INVENTION

Thus, in accordance with the present invention, there is provided a fusion protein comprising a drug-binding portion of a carrier polypeptide and a first cell-targeting peptide or protein. The carrier polypeptide may be an apoprotein, a binding protein or a natural or synthetic variant thereof, such as CagA or NscA. The binding protein may be a biosynthetic gene cluster protein, such as BlmA, PlmA or MRD, or a pathogen drug-resistance protein. The first cell-targeting peptide or protein may be a cancer cell targeting peptide or a tumor vasculature targeting peptide, for example, that targets a cancer cell such as is a pancreatic cancer cell, a liver cancer cell, a lymphoma cell, a myeloma cell, a neuroblastoma cell, a breast cancer cell, a prostate cancer, or a head & neck cancer cell. The fusion protein may further comprise a complexed drug, such as an antibiotic, a plant akyloid, an alkylating agent, a DNA repair inhibitor or a DNA cleaving agent. The DNA cleaving agent may, in particular, be an enediyne. The first cell-targeting peptide may be attached at the N-terminus of the carrier polypeptide, at the C-terminus of the carrier polypeptide, or attached internally to the carrier polypeptide. The fusion protein may comprise multiple copies of the cell-targeting peptide or protein, or may comprise a second cell-targeting peptide or protein.

In another embodiment, there is provided a nucleic acid encoding a drug-binding portion of a carrier polypeptide and a cell-targeting peptide or protein. The nucleic acid may further comprise a promoter, such as a prokaryotic promoter or a eukaryotic promoter. The nucleic acid may also further comprise one or more of a polyadenylation signal, an internal ribosome binding site, and a selectable marker. The carrier polypeptide may be an apoprotein, a binding protein or a natural or synthetic variant thereof, e.g., CagA, NscA, or a biosynthetic gene cluster protein, e.g., BlmA, PlmA or MRD, or a pathogen drug-resistance protein. The nucleic acid may further encode a cancer cell targeting peptide or protein or a tumor vasculature targeting peptide or protein. The drug may be selected from the group consisting of an antibiotic, a plant akyloid, an alkylating agent, a DNA repair inhibitor or a DNA cleaving agent. The cell-targeting peptide or protein is attached at the N-terminus, the C-terminus of the carrier polypeptide, or attached internally to the carrier polypeptide.

In yet another embodiment, there is provided a method of delivering a drug to a subject comprising administering to the subject a pharmaceutical composition comprising (a) a drug complexed with a fusion protein comprising a drug-binding portion of a carrier polypeptide and a cell-targeting peptide or protein; and (b) a pharmaceutically acceptable buffer or diluent. The carrier polypeptide may be an apoprotein, a binding protein or a natural or synthetic variant thereof. The apoprotein may be CagA or NscA. The binding protein may be a biosynthetic gene cluster protein, such as BlmA, PlmA or MRD, or a pathogen drug-resistance protein. The subject may be afflicted with cancer and the cell-targeting peptide targets cells or vasculature of the cancer. The cancer may be a pancreatic cancer, a liver cancer, a lymphoma, a myeloma, a neuroblastoma, a prostate cancer, a breast cancer, or a head & neck cancer. The drug may be selected from the group consisting of an antibiotic, a plant akyloid, an alkylating agent, a DNA repair inhibitor or a DNA cleaving agent. The cell-targeting peptide or protein may be attached at the N-terminus of the carrier polypeptide or at the C-terminus of the carrier polypeptide, or attached internally to the carrier polypeptide. The subject is a mammal, such as a human.

In still yet another embodiment, there is provided a method of screening for drug-binding activity in a carrier polypeptide comprising (a) contacting at least a drug-binding portion of a carrier polypeptide with a drug that is not a natural ligand for the carrier polypeptide; and (b) assessing binding of the drug to the drug-binding portion of a carrier polypeptide. The drug-binding portion may be fused to a cell-targeting peptide or protein. The drug may be labeled. Step (a) may be performed in the presence of a drug known to bind the carrier polypeptide, and the assay is a competitive assay. The carrier polypeptide may be an apoprotein, a binding protein or a natural or synthetic variant thereof. The apoprotein may be CagA or NscA. The binding protein may be a biosynthetic gene cluster protein, such as BlmA, PlmA or MRD, or a pathogen drug-resistance protein. The method may further comprise assessing binding affinity of the drug. The cell-targeting peptide or protein may be attached at the N-terminus of, the C-terminus of, or internally to the carrier polypeptide.

In an additional embodiment, there is provided a method of screening for drug-binding activity in a polypeptide comprising (a) providing at least a drug-binding portion of a carrier polypeptide; and (b) assessing binding of a selected drug to the drug-binding portion of a carrier polypeptide. The method may further comprise, prior to step (b), mutagenizing the drug-binding portion. The mutagenizing may be randomized or non-randomized. The method may also further comprise, following step (b), mutagenizing the drug-binding portion, and assessing binding of the selected drug to the mutagenized drug-binding portion. This mutagenizing may also be randomized or non-randomized. The carrier polypeptide may be an apoprotein, a binding protein or a natural or synthetic variant thereof, such as CagA or NscA. The binding protein may be a biosynthetic gene cluster protein, such as BlmA, PlmA or MRD, or a pathogen drug-resistance protein. The method may further comprising assessing binding affinity of the drug. The drug-binding portion may be fused to a cell-targeting peptide.

In still an additional embodiment, there is provided a method of producing a fusion protein-drug complex comprising (a) providing a host cell comprising a nucleic acid encoding a fusion protein comprising a drug-binding portion of a carrier polypeptide and a cell-targeting peptide or protein, wherein the host cell further produces the drug; and (b) culturing the host cell under conditions where both the fusion protein and the drug are produced. The method may further comprise purifying the complex. The host cell may be a prokaryotic cell, such as a bacterial cell, for example, one which naturally produces the drug and is knocked out for expression of natural carrier polypeptide. The host cell may also be a yeast cell. The nucleic acid may be stably transformed into the genome of the host cell. The carrier polypeptide may be an apoprotein, a binding protein or a natural or synthetic variant thereof. The cell-targeting peptide or protein may be attached at the N-terminus of, the C-terminus of, or internally to the carrier polypeptide.

In a further embodiment, there is provided a host cell comprising a nucleic acid encoding a fusion protein comprising a drug-binding portion of a carrier polypeptide and a cell-targeting peptide or protein. The host cell may further produce the drug. The cell-targeting peptide or protein may be attached at the N-terminus of, the C-terminus of, or internally to the carrier polypeptide.

As used herein the specification, "a" or "an" may mean one or more. As used herein in the claim(s), when used in conjunction with the word "comprising," the words "a" or "an" may mean one or more than one. As used herein "another" may mean at least a second or more.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIGS. 2A–B—(FIG. 2A) Sequences of the designed CTPs and (FIG. 2B) schematic representation of expression vectors pET14M/CTP (for N-His$_6$-tagged fusion protein) and pET37M/CTP (for C-His$_8$-tagged).

FIGS. 3A–D—Schematic representation of expression vectors for the two versions of N-His$_6$-tagged CTP-carrier protein fusion (FIG. 3A) and carrier protein-CTP fusion (FIG. 3B) (pET14M/CTP-based) and the two versions of C-His$_8$-tagged CTP-carrier protein fusion (FIG. 3C) and carrier protein-CTP fusion (FIG. 3D) (pET37M/CTP-based).

FIGS. 6A–D—Fluorescence images of CTP-targeted binding of apo-proteins or drug binding proteins to cancer cells. (FIG. 6A) BlmA with KS1617 cells: (I), native protein as a negative control, 10 min. incubation; (II) NGR-BlmA, 10 min. incubation; (III) NGR-BlmA, 60 min incubation. (FIG. 6B) NcsA with KS1617 cells: NcsA-NGR. (FIG. 6C) NcsA with WM115 cells (with various configuration as shown in FIG. 3): (I) RGD-NcsA-His$_8$ (C); (II) NcsA-RGD-His$_8$ (D); (III) His$_6$-RGD-NcsA (A); (IV) His$_6$-NcsA-RGD (B). (FIG. 6D) CagA: (I) His$_6$-CagA-NGR (B) with KS1617 cells; (II) His$_6$-CagA-RGD (B) with WM115 cells. See FIG. 3 for fusion configurations denoted as A, B, C, or D.

DETAILED DESCRIPTION OF THE INVENTION

I. The Present Invention

Figure 1:
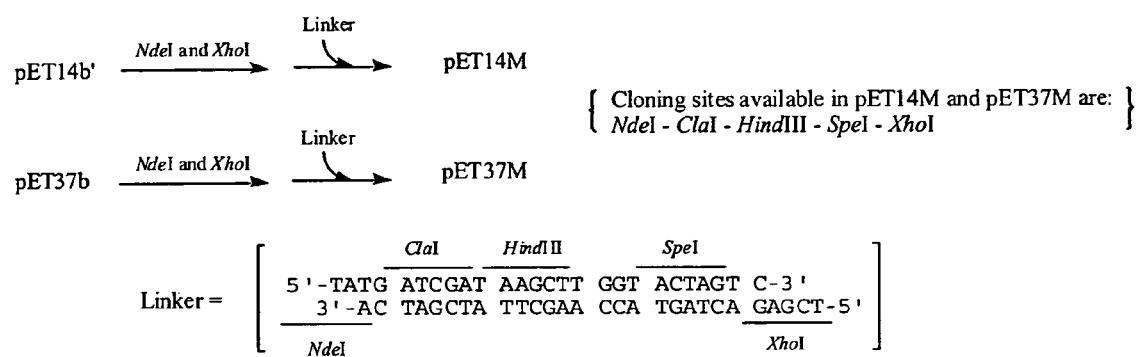
FIG. 1—Schematic representation of expression vectors pET14M and pET37M. Only selected restriction sites were shown.

The present invention utilizes a new approach in the modification and preparation of natural proteins for cancer therapy. This approach combines the advantages of potent cytotoxicity observed in natural chemopharmaceuticals, the proven selectivity and specificity of tumor targeting peptides, and the availability of naturally-occurring, drug-binding proteins. These molecules are described in greater detail below.

Thus, the present invention identifies naturally-occurring proteins that have the ability to bind toxic drugs in a reversable fashion. Examples of such proteins are the apoproteins and so-called "binding proteins" that are typically associated with biosynthetic pathways. Such naturally-occurring proteins may be used in their entirety, or the drug binding portions thereof identified and used as discrete entities. In addition, these molecules can be screened for binding to other drugs to which they do not normally bind. Finally, these molecules can be used as the platform for the creation of new, modified binding proteins with expanded drug binding capabilities.

A. Apoproteins

Apoproteins, with rare exceptions, are small, acidic proteins that exhibit high degrees of homology. They are encoded by preapoproteins with leader peptides of 32–34 amino acids. Examples include Ked, NcsA, McmA and AxnA. A generic structure for these molecules includes a seven-stranded anti-parallel β-barrel domain linked to a subdomain composed of two β-hairpin ribbons. It has been suggested that this motif resembles the variable domain of immunoglobulin. Functionally, these apoproteins have also been shown to exhibit a selective protease activity, suggesting a more active role in chemotherapeutic drug delivery.

Moreover, expression of some apoproteins is constitutive, and independent of chromophore production, thereby assuring that the chromophore is sequestered, and suggesting a role in self resistance.

The present invention seeks to take advantage of the drug-binding aspect of apoproteins. Because apoproteins are natural drug ligands, they have an inherent ability to binding certain kinds of drugs. An example is the binding of the C-1027 enediyne chromophore to the Cag-A apo-protein of *Streptomyces globisporous* or the NCS enediyne chromophore to the Ncs apoprotein in *Streptomyces carzinostaticus*. One of skill in the art may readily screen a wide variety of apoproteins for the ability to bind a particular drug, or conversely, screen a number of drugs for their ability to bind to a particular apoprotein. In addition, using molecular engineering techniques, one can modify the structure of a given apoprotein, thereby altering its drug-binding ability.

B. Binding Proteins

The term "binding proteins," in the context of the present invention, defines a series of naturally-occurring small molecules that are often associated with drug biosynthetic pathways. These molecules act as carriers for drugs produced by various organisms and, as such, are involved in drug sequestration, drug transport and drug resistance.

Just as with apoproteins, the present invention seeks to take advantage of the drug-binding capabilities of these proteins. An example of one such binding protein is BlmA, a bleomycin binding protein from *Streptomyces verticillus* (Sugiyama et al., 2002). Another example is the MRD protein, which binds mytomycin C, from *Streptomyces lavendulae* (Martin et al., 2002). Again, one may readily screen such binding proteins for the ability to bind a particular drug, screen a number of drugs for their ability to bind to a particular binding protein, or even create new binding proteins with distinct binding specificities using molecular engineering techniques.

II. Fusion Proteins

A. Fusion Types

Fusion proteins are a specific type of insertional mutant. As such, protein fusions thus comprise contiguous segments from at least two different proteins—in this case from a drug-binding protein and a cell-targeting peptide or protein. There are terminal fusions, where the contiguous segments are attached in an "end to end" fashion, and there are internal fusions, where a contiguous segment from one protein is inserted into a second contiguous segment. For the purposes of the present invention, a fusion protein will have at least 3 consecutive amino acid residues from two sources.

The contiguous segments of the fusion proteins described herein may come from a variety of sources. The first source is a natural drug-binding protein (e.g., an apoprotein or a biosynthetic cluster binding protein). However, the contiguous drug-binding segment may be modified from its natural state in order to alter its biological properties (half-life in vivo, drug-binding specificity, drug-binding affinity, etc.). All of the drug-binding protein may be used, or a drug-binding fragment thereof.

A second source for contiguous segments is a targeting peptide or protein. A targeting peptide or protein is one capable of binding, in a specific fashion, to a particular target ligand on a cell or tissue. Again, the entire protein may be utilized, but it may prove advantageous to use only that portion of the protein that directs its targeting. The protein may be modified as well to achieve varied targeting, but more likely the modifications would relate to the relative strength of ligand binding or stability.

Yet a third source for a contiguous segment is a synthetic molecule. As described elsewhere in this document, methods are provided for the identification of new proteins/segments with drug-binding and cell-targeting capabilities. As such, the ability to create totally new fusions is provided. For example, methods are known in the art to screen synthetic peptide libraries for binding to a target ligand. In addition, the present invention provides for methods of screening proteins (known and unknown) for drug-binding abilities.

B. Linkers/Coupling Agents

In an alternative embodiment, the "fusion" of protein segments is not achieved by a linear peptide bond, but instead by an chemical fusion, i.e., joining of a cell-targeting peptide to the drug-binding polypeptide by means that do not rely on a gene fusion. Typically, this will involve the use of a chemical linker. The linker can be attached to the N- or C-terminus of the molecule, or to an internal amino acid.

Peptide linkers may include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Additionally, while numerous types of disulfide-bond containing linkers are known which can successfully be employed to conjugate moieties, certain linkers will generally be preferred over other linkers, based on differing pharmacologic characteristics and capabilities. For example, linkers that contain a disulfide bond that is sterically "hindered" are to be preferred, due to their greater stability in vivo.

Cross-linking reagents are used to form molecular bridges that tie together functional groups of two different molecules, e.g., a stabilizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

TABLE 1

HETERO-BIFUNCTIONAL CROSS-LINKERS

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |

TABLE 1-continued

HETERO-BIFUNCTIONAL CROSS-LINKERS

| Linker | Reactive Toward | Advantages and Applications | Spacer Arm Length\after cross-linking |
|---|---|---|---|
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Non-selective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

SMPT is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak and Thorpe, 1986). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single-chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Homobifunctional amine crosslinkers include glutaraldehyde, bis(imido-esters), bis(succinimidyl-esters), diisocyanates and diacid chlorides. However, these reagents tend to yield high molecular weight aggregates, making them unsuitable for preparing conjugates between two different amine-containing biomolecules.

Other more sophisticated amine-reactive linkers, however, are available. These included the following: BASED, BSOCOES, Sulfo-BSOCOES, DMAI (DMA), DMSI (DMS), DMPI (DMP), DSS, Sulfo-DSS(BS3), DSSeb, Sulfo-DSSeb, DPDPB, DSG, DTSSP, DST, DTBP, DSP (Lomant's Reagent), Sulfo-HSAB, EGS, and Sulfo-EGS. These reagents are available from Pierce Biotechnology, Sigma-Aldrich and Uptima.

Various sulfur (thiol)-reactive linkers include $BM[PEO]_3$, $BM[PEO]_4$, BMB, BMDB, BMH, BMOE, DPDPB, DTME, and HBVS (Pierce Biotechnology).

C. Peptide Synthesis

In the context of linker fusions (above) and in screening (below), it may be useful to synthesize peptides de novo. Various automatic synthesizers are commercially available and can be used in accordance with known protocols. See, for example, Stewart and Young, (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, can be readily synthesized and then screened in screening assays designed to identify reactive peptides.

III. Nucleic Acids Encoding Fusions and Recombinant Production thereof

Certain embodiments of the present invention concern a nucleic acid encoding the fusion proteins of the present invention. The term "nucleic acid" is well known in the art, and will generally refer to a molecule (i.e., a strand) of DNA, RNA or a derivative or analog thereof. The term "nucleic acid" encompasses the terms "oligonucleotide" and "polynucleotide," each as a subgenus of the term "nucleic acid." The term "oligonucleotide" refers to a molecule of between about 3 and about 100 nucleotides in length. The term "polynucleotide" refers to a molecule of greater than about 100 nucleotides in length.

Thus, a nucleic acid may encompass a single-stranded or double-stranded molecule molecule that comprises a complementary strand(s) or "complement" of a particular sequence. As used herein, a single-stranded nucleic acid may be denoted by the prefix "ss," and a double-stranded nucleic acid by the prefix "ds."

In certain embodiments, the nucleic acid is a nucleic acid segment. As used herein, the term "nucleic acid segment," are smaller fragments of a nucleic acid, such as for non-limiting example, those that encode only part of the peptide or polypeptide sequence. Thus, a "nucleic acid segment" may comprise any part of a gene sequence, of from about 10 nucleotides to the full length of the peptide or polypeptide encoding region.

A. Preparation and Purification of Nucleic Acids

A nucleic acid may be made by any technique known to one of ordinary skill in the art, such as for example, chemical synthesis, enzymatic production or biological (recombinant) production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al. (1986) and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al., 1989, incorporated herein by reference). In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

B. Hybridization

As used herein, "hybridization" is understood to mean the forming of a double or triple stranded molecule or a molecule with partial double or triple stranded nature. The term "anneal" as used herein is synonymous with "hybridize." As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

C. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACS). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 2 lists non-limiting examples of elements/promoters that may be employed, in the context of the present invention, to regulate the expression of a RNA. Table 3 provides non-limiting examples of inducible elements, which are regions of a nucleic acid sequence that can be activated in response to a specific stimulus.

TABLE 2

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ α and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |

TABLE 2-continued

Promoter and/or Enhancer

| Promoter/Enhancer | References |
|---|---|
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $\alpha_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |

TABLE 3-continued

Inducible Elements

| Element | Inducer | References |
| --- | --- | --- |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have promise as delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid (e.g., one encoding a gene of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

D. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989; Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789, 215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322, 783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for tranfecting vascular cells and tissues removed from an organism in an ex vivo setting are known to those of skill in the art. For example, canine endothelial cells have been genetically altered by retroviral gene transfer in vitro and transplanted into a canine (Wilson et al., 1989). In another example, yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the nucleic acids of the present invention. In particular aspects, the transplanted cells or tissues may be placed into an organism. In preferred facets, a nucleic acid is expressed in the transplanted cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

c. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

e. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK$^-$ fibroblasts have been transfected with the thymidine kinase gene by sonication loading (Fechheimer et al., 1987).

g. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

h. Receptor-Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

i. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed," i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

G. Cell-Based Production

Cells may be propagated using a variety of techniques well known to those of skill in the art. For example, cells of the present invention may be propagated as non-anchorage dependent cells growing freely in suspension throughout the bulk of the culture; or as anchorage-dependent cells requiring attachment to a solid substrate for their propagation (i.e., a monolayer type of cell growth). WO publication numbers WO 97/26334 (published Jul. 24, 1997) and WO 97/26321 (published Jul. 24, 1997) are specifically incorporated herein by reference and describe the different modes of cell culture.

In particular embodiments, the cells may be propagated in a microcarrier culture (van Wezel, 1967). This mode of the culture propagation on the microcarriers makes it possible to use this system for cellular manipulations, such as cell transfer without the use of proteolytic enzymes, cocultivation of cells, transplantation into animals, and perfusion of the culture using decanters, columns, fluidized beds, or hollow fibers for microcarrier retainment.

H. Purification

The present invention also provides purified, and in preferred embodiments, substantially purified, proteins, polypeptides, or peptides. The term "purified proteins, polypeptides, or peptides" as used herein, is intended to refer to an proteinaceous composition, isolatable from mammalian cells or recombinant host cells, wherein the at least one protein, polypeptide, or peptide is purified to any degree relative to its naturally-obtainable state, i.e., relative to its purity within a cellular extract. A purified protein, polypeptide, or peptide therefore also refers to a wild-type or mutant protein, polypeptide, or peptide free from the environment in which it naturally occurs.

Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present invention provides DNA sequences for the specific proteins, any fusion protein purification method can now be practiced. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

Any of a wide variety of procedures may be employed for purification of proteins. For example, thin layer chromatography, gas chromatography, high performance liquid chromatography, paper chromatography, affinity chromatography or supercritical flow chromatography may be used to effect separation of the proteins according to the present invention.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

IV. Targeting Peptides or Polypeptides

The following table provides a listing of exemplary peptide sequences useful in targeting of tumors and tumor vasculature in accordance with the present invention.

TABLE 4

Cancer Cell Surface or Cancer-Related Targeting Peptides Identified by Phage-Display Library

| Peptide Ligand | Cellular Target | Ref. |
|---|---|---|
| Tumor cell surface | | |
| KNGPWYAYTGRO (SEQ ID NO:1) | Surface idiotype of SUP-88 human B-cell lymphoma | Renschler et al., 1994 |
| NWAVWXKR, (SEQ ID NO:2) | | |
| YXXEDLRRR (SEQ ID NO:3) | | |
| XXPVDHGL (SEQ ID NO:4) | | |
| LVRSTGQFV, (SEQ ID NO:5) | Surface idiotype of human chronic lymphocytic lymphoma (CLL) | Buhl et al., 2002 |
| LVSPSGSWT (SEQ ID NO:6) | | |
| ALRPSGEWL (SEQ ID NO:7) | | |
| AIMASGQWL (SEQ ID NO:8) | | |
| QILASGRWL, (SEQ ID NO:9) | | |
| RRPSHAMAR (SEQ ID NO:10) | | |
| DNNRPANSM, (SEQ ID NO:11) | | |
| LQDRLRFAT (SEQ ID NO:12) | | |
| PLSGDKSST (SEQ ID NO:13) | | |
| FDDARL (SEQ ID NO:14) | Human multiple myeloma M-protein | Szecsi et al., 1999 |
| FSDARL, (SEQ ID NO:15) | | |
| FSDMRL (SEQ ID NO:16) | | |
| FVDVRL, (SEQ ID NO:17) | | |

TABLE 4-continued

Cancer Cell Surface or Cancer-Related Targeting Peptides Identified by Phage-Display Library

| Peptide Ligand | Cellular Target | Ref. |
|---|---|---|
| FTDIRL, (SEQ ID NO:18) | | |
| FNDYRL (SEQ ID NO:19) | | |
| FSDTRL, (SEQ ID NO:20) | | |
| PIHYIF, (SEQ ID NO:21) | | |
| YIHYIF, (SEQ ID NO:22) | | |
| RIHYIF (SEQ ID NO:23) | | |
| IELLQAR (SEQ ID NO:24) | HL 60 human lymphoma & B-16 mouse melanoma | Fukuda et al., 2000 |
| CVFXXXYXXC (SEQ ID NO:25) | Prostate-specific antigen (PSA) | Wu et al., 2000 |
| CXFXXXYXYLMC (SEQ ID NO:26) | | |
| CVXYCXXXXCYVC (SEQ ID NO:27) | | |
| CVXYCXXXXGWXC (SEQ ID NO:28) | | |
| DPRATPGS (SEQ ID NO:29) | LNCaP prostate cancer | Romanov et al., 2001 |
| HLQLQPWYPQIS (SEQ ID NO:30) | WAG-2 human neuroblastoma | Zhang et al., 2001 |
| VPWMEPAYQRFL (SEQ ID NO:31) | MDA-MB435 breast cancer | Zhang et al., 2001 |
| TSPLNTHNGQKL (SEQ ID NO:32) | Head and neck cancer lines | Hong and Clayman, 2000 |
| OSPL W/F, R/K, N/H, S, V/H, L RLTGGKGVG (SEQ ID NO:33) | ECV304 endothelial cell line Hep-2 human larygeal carcinoma | Ivanenko et al., 1999 Ivanenko et al., 1999 |
| Tumor vasculature | | |
| CDCRGDCFC (RGD-4C) (SEQ ID NO:34) | $\alpha_v\beta_3$, $\alpha_v\beta_5$ | Koivunen et al., 1995 |
| ACDCRGDCGCG (SEQ ID NO:35) | $\alpha_v\beta_5$, $\alpha_v\beta_3$ | Assa-Munt et al., 2001 |
| CNGRCVSGCAGRC (SEQ ID NO:36) | Aminopeptidase N | Pasqualini et al., 2000 |
| CNGRC (SEQ ID NO:37) | Aminopeptidase N | |
| CVCNGRMEC, (SEQ ID NO:38) | | |
| NGRAHA (SEQ ID NO:39) | | |
| TAASGVRSMH, (SEQ ID NO:40) | NG2 proteoglycan | Burg et al., 1999 |
| LTLRWVGLMS (SEQ ID NO:41) | | |
| CGSLVRC, (SEQ ID NO:42) | Vasculature of various tumors | Arap et al., 1998 |
| CGLSDSC (SEQ ID NO:43) | | |
| NRSLKRISNKRIRRK, (SEQ ID NO:44) | IC-12 rat trachea | Kenel et al., 2000 |
| LRIKRKRRKRKKTRK, (SEQ ID NO:45) | | |
| NRSTHI (SEQ ID NO:46) | | |
| SMSIARL (SEQ ID NO:47) | Mice prostate | Arap et al., 2002 |
| VSFLEYR (SEQ ID NO:48) | | |
| CPGPEGAGC (SEQ ID NO:49) | Aminopeptidase P | Essler et al., 2002 |

TABLE 4-continued

Cancer Cell Surface or Cancer-Related Targeting Peptides Identified by Phage-Display Library

| Peptide Ligand | Cellular Target | Ref. |
|---|---|---|
| ATWLPPR (SEQ ID NO:50) | VEGF | Binetruy-Tournaire et al., 2000 |
| RRKRRR (SEQ ID NO:51) | VEGF | Bae et al., 2000 |
| ASSSYPLIHWRPWAR (SEQ ID NO:52) | VEGF | Asai et al., 2002 |
| CTTHWGFTLC (SEQ ID NO:53) | Gelantinase | Koivunen et al., 1999 |

V. Chemotherapeutics

In accordance with the present invention, a wide variety of chemotherapeutic agents can be utilized. These can be, for example, agents that directly cross-link DNA, agents that intercalate into DNA, agents that lead to chromosomal and mitotic aberrations by affecting nucleic acid synthesis, and agents that damage DNA (including compounds that interfere with DNA replication, mitosis, and chromosomal segregation).

A. Antibiotics

Doxorubicin. Doxorubicin hydrochloride, 5,12-Naphthacenedione, (8s-cis)-10-((3-amino-2,3,6-trideoxy-a-L-lyxo-hexopyranosyl)oxy)-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m² at 21-day intervals or 25 to 30 mg/m² on each of 2 or 3 successive days repeated at 3- or 4-wk intervals or 20 mg/m² once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m² in patients with normal heart function and 400 mg/m² in persons having received mediastinal irradiation. Alternatively, 30 mg/m² on each of 3 consecutive days, repeated every 4 wk. Exemplary doses may be 10 mg/m², 20 mg/m², 30 mg/m², 50 mg/m², 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Daunorubicin. Daunorubicin hydrochloride, 5,12-Naphthacenedione, (8S-cis)-8-acetyl-10-((3-amino-2,3,6-trideoxy-a-L-lyxo-hexanopyranosyl)oxy)-7,8,9,10-tetrahydro-6,8,11-trihydroxy-10-methoxy-, hydrochloride; also termed cerubidine and available from Wyeth. Daunorubicin intercalates into DNA, blocks DNA-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (about 40%). Dosage must be reduced in liver or renal insufficiencies.

Suitable doses are (base equivalent), intravenous adult, younger than 60 yr. 45 mg/m²/day (30 mg/m² for patients older than 60 yr.) for 1, 2 or 3 days every 3 or 4 wk or 0.8 mg/kg/day for 3 to 6 days every 3 or 4 wk; no more than 550 mg/m² should be given in a lifetime, except only 450 mg/m² if there has been chest irradiation; children, 25 mg/m² once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m², 20 mg/m², 30 mg/m², 50 mg/m², 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Mitomycin. Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D. Actinomycin D (Dactinomycin) (50-76-0); $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Bleomycin. Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

B. Miscellaneous Agents

Cisplatin. Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

In certain aspects of the current invention cisplatin is used in combination with emodin or emodin-like compounds in the treatment of non-small cell lung carcinoma. It is clear, however, that the combination of cisplatin and emodin and or emodin-like compounds could be used for the treatment of any other neu-mediated cancer.

VP16. VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Enediynes. Neocarzinostatin (NCS), the first member of the enediyne family of antitumor antibiotics, was originally discovered as a macromolecular antitumor antibiotic from the culture filtrates of a *Streptomyces carzinostaticus* strain in Ishida et al. (1965). Although it became clear shortly after its discovery that all biological activities of NCS resided in a non-protein chromophore, the NCS chromophore structure was not elucidated until Edo et al. (1985), revealing an unprecedented bicyclo[7,3,0]dodecadiynene system, i.e., the 9-membered enediyne core, decorated with an aminosugar and a naphthoic acid moiety. However, this seminal work was underappreciated in the subsequent two years, and it was the discovery of the calicheamicins from a *Micromonospora echinospora* strain (Lee et al., 1987a; Lee et al., 1987b) and the esperamicins from an *Actinomadura verrucosospora* strain (Golik et al., 1987a; Golik et al., 1987b) in 1987 that grabbed the attention of chemists and biologists alike with respect to the enediynes. In contrast to NCS, the structural elucidation of these latter compounds unveiled a novel bicyclo[7,3,1]tridecadiynene system, i.e., the 10-membered enediyne core, decorated with several deoxysugar moieties. Since then, the enediyne family of natural products has been the focus of intense research activity in the fields of chemistry, biology, and medical sciences because of their highly unusual molecular architectures, biological activities, and modes of actions (Nicolaou et al., 1991; Doyle and Border, 1995; Smith and Nicolaou, 1996; Maeda et al., 1997; Xi and Goldberg, 1999; Thrson et al., 2000; Jones and Fouad; 2002).

Over twenty enediyne natural products are currently known, and new members of the enediyne family are continuously discovered with the newest addition, the shishijimicins from a marine ascidian *Didemmum proliferum* species, reported in early 2003 (Oku et al., 2003). The enediyne natural products could be classified into two subchromoproteins consisting of an apoprotein and the enediyne chromophore, with N1999A2 from *Streptomyces* sp. AJ9493 as the only exception that was isolated as a chromophore alone (Ando et al., 1998). The apoprotein acts as a stabilizer and specific carrier for the otherwise unstable chromophore and its transport and interaction with target DNA. Due to their intrinsic reactivity, only three other chromoprotein chromophore structures, in additional to the NCS chromophore and N1999A2, are currently known—kedarcidin from *Actinomycete* L585-6 (Leet et al., 1992), C-1027 from *Streptomyces globisporus* Minami et al., 1993; Yoshida et al., 1993; Iida et al., 1996; Otani et al., 1999), maduropeptin from *Actinomadura madurae* (Schroeder et al., 1994). Members of the 10-membered enediyne core sub-category are in general more stable, all of which were isolated as discrete small molecules. In addition to the calcicheamicins, esperamicins and shishijimicins, other members of this sub-category whose structures have been elucidated include dynemicin, from *Micromonospora chersina* sp. nov. No. M965-1 (Konishi et al., 1989; Myers et al, 1995), and namenamicin, from a marine ascidian *Polysyncraton lithostrotum* species (McDonald et al., 1996).

Members of both sub-categories of enediynes share a common mechanism of action, despite their structural difference. The enediyne core undergoes an electronic rearrangement (Bergman or Myers rearrangement) to form a transient benzenoid diradicals that damage DNA by abstracting hydrogen atoms from the deoxyribose moiety on both strands. Subsequent reactions of the resultant deoxyribose carbon-centered radicals with molecular oxygen initiate a process that leads in both single-strand and double-strand DNA cleavage (Nicolaou et al., 1991; Doyle and Border, 1995; Smith, and Nicolaou, 1996; Maeda et al., 1997; Xi and Goldberg, 1999; Thrson et al., 2000; Jones and Fouad, 2002; Stassinopoulos et al., 1996; Ikemoton et al., 1995; Dedon and Goldberg, 1992). This novel mechanism of DNA damage has important implications for the development of the enediynes into clinical anticancer drugs (Stassinopoulos et al., 1996; Ikemoton et al., 1995; Dedon and Goldberg, 1992; Sugiura et al., 1990; Zein et al., 1993; Nicolaou et al., 1993; Kappen and Goldberg, 1994; Yu et al., 1994; Hensens et al., 1994; Ho et al., 1994; Schor et al., 1999; Dziegielewski and Beerman, 2002).

Although the natural enediynes have seen limited use as clinical drugs mainly because of substantial toxicity, various polymer-based delivery systems or enediyne antibody conjugates have shown great clinical success and/or promise in anticancer chemotherapy (Doyle and Border, 1995; Maeda et al., 1997; Thrson et al., 2000; Jones and Fouad, 2002; Sielvers et al., 1999; Brukner, 2000). For example, the poly(styrene-co-maleic acid)-conjugated NCS was approved in Japan in 1993 and has been marketed since 1994 for use against hepatoma (Maeda et al., 1997). A CD33 monoclonal antibody (mAB)-calicheamicin conjugate was approved in the U.S. in 2000 and has been marketed under the trade name of Mylotar® to treat acute myeloid leukemia (Sielvers et al., 1999). Several antiheptoma mAB-C-1027 conjugates have also been prepared and show high tumor specificity and to exert a strong inhibitory effect on the growth of established tumor xenografts (Brukner, 2000). These examples clearly demonstrate that the enediynes can be developed into powerful drugs when their potent cytotoxicity is harnessed and delivered onto the target tumor cells.

Access to complex natural products such as the enediynes and their analogs by total synthesis poses a monumental challenge to synthetic chemists, and yet a tour de force effort by synthetic chemists has led to the total syntheses of almost every member of the enediyne family of natural products as well as a myriad of analogs. Significant progress made towards (a) improving cancer cell specificity, (b) developing efficient delivery systems to the tumor targets, and (c) designing triggers and trapping the enediynes as prodrugs (Xi and Goldberg, 1999; Thrson et al., 2000; Jones and Fouad, 2002). However chemical total synthesis has very limited practical value for complex natural products such as the enediynes, and analog generation by chemical modification of the natural products can only access to limited functional groups, often requiring multiple protection and deprotection steps.

Complementary to organic synthesis, genetic manipulations of genes governing secondary metabolism—an emerging technology also known as combinatorial biosynthesis—offer a promising alternative to preparing complex natural products and their analogs biosynthetically (Hopwood, 1997; Cane et al., 1998; Shen, 2000; Staunton and Wessman, 2001; Strohl, 2001; Du and Shen, 2001; Rodriguez and McDaniel, 2001; Walsh, 2002). Specific structural alteration in the presence of other functional groups can often be achieved, and the target molecules will be produced by a recombinant organism that is amenable for large-scale fermentation, thereby lowering the production cost and reducing the environment concern associated with conventional chemical synthesis. The success of this approach depends on (a) the cloning and genetic and biochemical characterization of the biosynthetic pathways of the target metabolites and (b) the development of strategies, methods, and expedient tools for combinatorial manipulation of natural product biosynthetic gene clusters.

C. Plant Alkyloids

Taxol. Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Vincristine. Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisolone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine. When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

D. Alkylating Agents

Carmustine. Carmustine (sterile carmustine) is one of the nitrosoureas used in the treatment of certain neoplastic diseases. It is 1,3bis(2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject Melphalan. Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-(bis(2-chloroethyl)amino)-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide. Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride ((ClCH$_2$CH$_2$)$_2$N—POCl$_2$) in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil. Chlorambucil (also known as leukeran) is a bifunctional alkylating agent of the nitrogen mustard type that has been found active against selected human neoplastic diseases. Chlorambucil is known chemically as 4-(bis(2-chlorethyl)amino) benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan. Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine. Lomustine is one of the nitrosoureas used in the treatment of certain neoplastic diseases. It is 1-(2-chloroethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 $mg/m^2$ to 100 $mg/m^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 $mg/m^2$ as a single oral dose every 6 weeks. In individuals with compromised bone marrow function, the dose should be reduced to 100 $mg/m^2$ every 6 weeks. When lomustine is used in combination with other myelosuppressive drugs, the doses should be adjusted accordingly. It is understood that other doses may be used for example, 20 $mg/m^2$ 30 $mg/m^2$, 40 $mg/m^2$, 50 $mg/m^2$, 60 $mg/m^2$, 70 $mg/m^2$, 80 $mg/m^2$, 90 $mg/m^2$, 100 $mg/m^2$, 120 $mg/m^2$ or any doses between these figures as determined by the clinician to be necessary for the individual being treated.

VI. Screening Assays

A. Assay Formats

The present invention further comprises methods for identifying drug binding proteins and drug binding activity in proteins of interest. These assays may comprise random screening of large libraries of polypeptides—natural, synthetic or mutagenized; alternatively, the assays may be used to focus on particular classes of proteins with an eye towards structural attributes that are believed to make them more likely to bind a drug of interest, with or without additional modification. It will, of course, be understood that all the screening methods of the present invention are useful in themselves notwithstanding the fact that a protein with a given binding specificity may not be found. The invention provides methods for screening for such candidates, not solely methods of finding them.

A quick, inexpensive and easy assay to run is an in vitro binding assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

For example, binding of a drug to a target protein may be assessed either free in solution, fixed to a support, expressed in or on the surface of a cell. Either the target protein or the drug may be labeled, thereby permitting determining of binding. Competitive binding formats can be performed in which one of the agents is labeled, and one may measure the amount of free label versus bound label to determine the effect on binding. A technique for high throughput screening of compounds is described in WO 84/03564. Large numbers of small peptide test compounds are synthesized on a solid substrate, such as plastic pins or some other surface. Bound polypeptide is detected by various methods.

Additional assays may be performed to measuring strength of binding, the ability of the protein to dissociate the drug under in cyto and in vivo conditions, clearance of the complex or carrier, as well as for potential toxicity.

B. Mutagenesis

Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

a. Random Mutagenesis

1. Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al. 1991). Insertion mutagenesis has been very successful in bacteria and *Drosophila* (Cooley et al. 1988) and recently has become a powerful tool in corn (Schmidt et al. 1987); *Arabidopsis*; (Marks et al., 1991; Koncz et al. 1990); and *Antirrhinum* (Sommer et al. 1990).

Transposable genetic elements are DNA sequences that can move (transpose) from one place to another in the genome of a cell. The first transposable elements to be recognized were the Activator/Dissociation elements of *Zea mays*. Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. these terminal inverted repeats may be anything from a few bases to a few hundred bases long and in many cases they are known to be necessary for transposition.

Prokaryotic transposable elements have been most studied in *E. coli* and Gram negative bacteria, but also are present in Gram positive bacteria. They are generally termed insertion sequences if they are less than about 2 kB long, or transposons if they are longer. Bacteriophages such as mu and D108, which replicate by transposition, make up a third type of transposable element. elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Eukaryotic elements also can be classified according to their structure and mechanism of transportation. The primary distinction is between elements that transpose via an RNA intermediate, and elements that transpose directly from DNA to DNA.

Elements that transpose via an RNA intermediate often are referred to as retrotransposons, and their most characteristic feature is that they encode polypeptides that are believed to have reverse transcriptionase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

2. Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

3. Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2–9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

4. In Vitro Scanning Mutagenesis

Random mutagenesis also may be introduced using error prone PCR (Cadwell and Joyce, 1992). The rate of mutagenesis may be increased by performing PCR in multiple tubes with dilutions of templates. One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham and Wells, 1989).

Techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

5. Random Mutagenesis by Fragmentation and Reassembly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

b. Site-Directed Mutagenesis

Structure-guided site-specific mutagenesis represents a powerful tool for the dissection and engineering of protein-ligand interactions (Wells, 1996; Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as E. coli polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as E. coli cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Burton and Barbas, 1994; Yelton et al., 1995; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis. Other methods of site-directed mutagenesis are disclosed in U.S. Pat. Nos. 5,220,007; 5,284,760; 5,354,670; 5,366,878; 5,389,514; 5,635,377; and 5,789,166.

VII. Drug Complexing

Various approaches may be utilized for preparation of drug complexes according to the present invention. For the chromoprotein antitumor antibiotics such as C-1027 and NCS, these can be produced directly in the designed recombinant organisms and isolated as the chromoproteins, i.e., drug-protein complex consisting of the enediyne chromophore and the apo-protein with the designed cancer-targeting peptides. For example, the apoprotein may be deleted from the native producer organism, and a genetically engineered gene with the desired cancer-targeting peptide fused at either N- or C-terminus or inserted in the middle of the apoprotein (either one or multiple copies of the cancer-targeting peptide) will be incorporated into an expression vector under the control of a strong promoter. The expression construct is then introduced into strain by appropriate methods. The chromoprotein complex will then be produced, isolated, and purified.

Alternatively, the drug molecule and the drug binding protein will be purified separately (i.e., from separate organisms), and reconstituted from the individually purified molecules in vitro, for examples, as described for the formation of the BlmA-bleomycin complex (Sugiyama et al., 2002). Briefly, the BlmA incorporated cancer-targeting peptides were overproduced using an E. coli host vector system and purified. The purified BlmA was then dissolved in a 10 mM sodium phosphate buffer (pH 7.2) and incubated with 10-fold molar excess of bleomycin A2 sulfate for 1 hr at room temperature. This molar ratio of bleomycin A2 was suitable for complete binding of BlmA, and will be optimized for BlmA variants.

Another example involves the expression of the mitomycin binding protein MRD and its variants incorporated with cancer-targeting peptides. The production, isolation, and purification of the resultant MRD proteins, and the formation of mitomycin binding protein MRD-mitomycin complexes could be carried out essentially according to the established procedures (Martin et al., 2002).

VIII. Pharmaceutical Formulations and Routes of Administration

For in vivo application, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts and buffers to render agents stable and allow for administration to subjects. Buffers also will be employed as appropriate.

Aqueous compositions of the present invention comprise an effective amount of the fusion protein-drug complex, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the agents of the present invention, its use in therapeutic compositions is contemplated. Supplementary active ingredients also can be incorporated into the compositions.

Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intratumoral, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Expression Vectors for Overproduction of the Drug Carrier Proteins in *E. coli*—Vectors with N-His$_6$- or C-His$_8$-tag Overexpression vectors were constructed from the commercially available pET14b (N-His$_6$-tag) and pET37b (C-His$_8$-tag) vectors (Novagen, Madison, Wis.). The HindIII and EcoRI sites of pET14b were abolished by digestion and blunt ligation to generate pET14b'. pET14b' and pET37b were then digested with NdeI and XhoI and ligated with an oligonucleotide containing the common cloning sites to yield the designed vectors pET14M and pET37M, respectively (FIG. 1).

Example 2

Selection of Drug Carrier Proteins and CTPs

The inventor chose two apo-proteins, CagA for C-1027 and NcsA for neocarzinostatin (NCS). C-1027 and NCS are examples of the chromoprotein enediyne family of anticancer antibiotics that are the most potent anticancer agents known to date. Both of them are isolated as chromoproteins, consisting of the enediyne chromophore and an apo-protein, and the chromoproteins are used directly as drugs. He cloned and sequenced the biosynthetic gene clusters of C-1027 from *Streptomyces globisporus* and for NCS from *Streptomyces carzinostaticus*, respectively. The C-1027 apo-protein is encoded by the cagA gene, while the NCS apo-protein is encoded by the ncsA gene.

Three drug binding proteins were chosen: BlmA for bleomycin (BLM), PlmA for phleomycin (PLM), and Mrd for mitomycin (MTM). BLM is a clinical anticancer drug marketed under the trade name of Blenoxane®. While it is incorporated into current therapy of several malignancies and is very effective, wide application of this agent has been prevented mainly by the dose-limiting pulmonary toxicity. The inventor cloned and sequenced the BLM biosynthetic gene cluster from *Streptomyces verticillus* and established that the blmA gene encodes the BLM-binding protein, BlmA, which forms a tight protein-drug complex with BLM. PLM is another member of the BLM family of anticancer antibiotics. He also cloned and sequenced the PLM biosynthetic gene cluster from *Streptomyces flavoviridis*, and the plmA gene that encodes the PLM-binding protein has been identified within the PLM cluster. The MTMs are natural products that contain a variety of functional groups, including aminobenzoquinone- and aziridine-ring systems. MTM C was the first recognized bioreductive alkylating agent and has been widely used clinically for various anticancer therapy. The mrd gene that has been cloned from the MTM C producing strain *Streptomyces lavendulae* encodes the MTM C-binding protein. Purified Mrd was shown to function as a drug-binding protein that provides protection against crosslinking of DNA by preventing reductive activation of MTM C.

The inventor chose three CTPs: CNGRC (NGR) for aminopeptidase N (CD13), CDCRGDCFC (RGD) (SEQ ID NO:34) for $\alpha_v\beta_3$ integrin, and SMSIARL (SMS) (SEQ ID NO:47) for targeting prostate cancer.

CNGRC (NGR) (SEQ ID NO:37) has been coupled to anticancer agent doxorubicin (DOX), and the resultant drug-CTP conjugates showed enhance drug efficacy against human breast cancer xenografts in nude mice and reduced toxicity compared with free DOX. It has also been coupled to a pro-apoptotic peptide that induces programmed cell death by membrane disruption. CNGRC was also coupled to tumor necrosis factor (TNF) α of mice and human, which showed 12–15 or 30 times enhancement of TNF efficacy in lymphoma and melanoma mice model. The receptor of CNGRC in tumor vasculature is aminopeptidase N (CD13), which is up regulated in endothelial cells within mice and human tumors. Recent finding suggests that different isoforms of CD13 are expressed in myeloid cells, epithelia and tumor associated blood vessels. CNGRC can only bind to the CD13 isoform expressed in tumors, which explained the selectivity and the tumor homing properties of NGR-drug conjugates.

CDCRGDCFC (RGD) (SEQ ID NO:34) contains the $\alpha_v\beta_3$ integrin binding Arg-Gly-Asp motif and binds to human $\alpha_v\beta_3$ integrins that are selectively expressed in human tumor blood vessels. RGD has been coupled to DOX and apoptotic peptide, and the resultant conjugates showed enhanced drug efficacy in human breast cancer xenografts in nude mice compared with free DOX and apoprotic peptide.

SMSIARL (SMS) (SEQ ID NO:47) selectively targets to prostates cancers 10–15 times higher than to other organs. When SMS was linked to a pro-apoptotic peptide that disrupts mitochondria membranes, it caused tissue disruption and delayed development of the prostate cancer in prostate cancer-prone transgenic mice.

The reason tumor vasculature ligands were chosen was because the rate of tumor growth is largely limited by blood supply. Angiogenesis not only allows the tumor to increase in size, but is also represents the means by which tumor metastasizes. Unlike tumor cells that constantly undergo mutations, tumor vasculature is genetically stable. Partial denuding of endothelium could lead to the formation of a thrombus in the tumor-feeding blood vessel leading to tumor regression.

Example 3

Construction of Expression Vectors for Overproduction of His-Tagged, CTP-Drug Carrier Protein Fusion Proteins in E. coli The three CTPs were synthesized flanking with the HindIII and EcoRI/SpeI sites at 5'-and 3'-ends, respectively (FIG. 2A). pET14M and pET37M (FIG. 1) were digested with HindIII and SpeI and ligated with the three CTP oligonucleotides to generate three pET14M/CTP vectors (N-His$_6$-tagged) and three pET37M/CTP (C-His$_8$-tagged), respectively (FIG. 2B).

Example 4

Cloning by PCR Genes Encoding the Apo-Proteins or Drug-Binding Proteins

The cagA gene was amplified by PCR from a cosmid harboring the C-1027 biosynthetic gene cluster using a forward primer 5'-TCCATATGGAATTCGCGCCCGCC-TTCTCC-3' (the EcoRI and NdeI sites are underlined) (SEQ ID NO:54) and a reverse primer, 5'-TTCTCGAGAAGCTTTCACGGCTTGGTCAG-3' (The HindIII and XhoI sites are underlined) SEQ ID NO:55.

The ncsA gene was amplified by PCR from a cosmid harboring the NCS biosynthetic gene cluster using forward a primer 5'-TCCATATGGAATTCGCGCGCCGACGGC-3' (SEQ ID NO:56) (the EcoRI and NdeI sites are underlined) and a reverse primer 5'-TTCTCGAGAAGCTTTCAGT-TGAAGGAGATCGC-3' (SEQ ID NO:57) (the HindIII and XhoI sites are underlined).

The blmA gene was amplified by PCR from pBS11 using a forward primer 5'-GTAGAATTCCATATGGTGAAAT-TCTTGGTTGCCG-3' (SEQ ID NO:58) (the EcoRI and NdeI sites are underlined) and a reverse primer 5'-GAT CTCGAGAAGCTTCTCCCCGCGGTGAAGTG-3' (SEQ ID NO:59) (the XhoI and HindIII sites are underlined).

The plmA gene was amplified by PCR from a plasmid containing a 1.4-kb SalI-PstI fragment harboring plmA using a forward primer 5'-GTAGAATTCCATATGGCCG-TATTGCTCTCG-3' (SEQ ID NO:60) (the EcoRI and NdeI sites are underlined) and a reverse primer 5'-GAT CTCGAGAAGCTTACGAACCGTCCGGGTCGT-3' (SEQ ID NO:61) (the XhoI and HindIII sites are underlined).

The mrd gene was amplified by PCR from the genomic DNA of the MTM C producing S. lavendulae using a forward primer 5'-CTAGAATTCCATATGTCAGCAAG-GATTTCCCTCTTC-3' (SEQ ID NO:62) (the EcoRI and NdeI sites are underlined) and a reverse primer 5'-GATCTCGAGAAGCTTCGGGAGGGGCGCGAAGAG-3' (SEQ ID NO:63) (the XhoI and HindIII sites are underlined).

The resultant PCR™ products were cloned into pGEM T-easy or pGEM-11zf vectors and sequenced to confirm PCR fidelity.

Example 5

Construction of Expression Vectors for Overproduction of His-Tagged, CTP-Drug Carrier Protein Fusion Proteins in E. coli The PCR-amplified fragments encoding various carrier proteins were digested with NdeI and HindIII and cloned into the same sites of pET14M/CTP (FIG. 3B) or pET37M/CTP (FIG. 3D) to yield two versions of the His-tagged, CTP and carrier protein fusion, respectively. Alternatively, the PCR-amplified fragments were similarly digested with EcoRI and XhoI and cloned into the same sites of pET14M/CTP (FIG. 3A) or pET37M/CTP (FIG. 3C) to yield two additional versions of the His-tagged, CTP and carrier protein fusion, respectively.

Example 6

Overproduction and Purification of His-Tagged, CTP-Drug Carrier Protein Fusion Proteins Overproduced in E. coli The overexpression constructs were introduced into E. coli B121(DE3) (Novagen) by transformation according to the protocols recommended by the manufacturer. Thus, a single colony was inoculated into 2 ml of LB medium with appropriate antibiotics (ampicillin 100 μg/ml for pET14M/CTP-based constructs or kanamycin 50 μg/ml for pET37M/CTP-based constructs (see FIG. 3). After overnight growth, 20 μl of culture was inoculated into 10 ml of LB and grew overnight. The culture was inoculated into 500 ml of LB and grew to O.D. 0.4–0.6 before induction. The production was induced by adding IPTG to 50–100 μg/ml and grew for 6–12 hrs before harvesting the cells.

Figure 4:
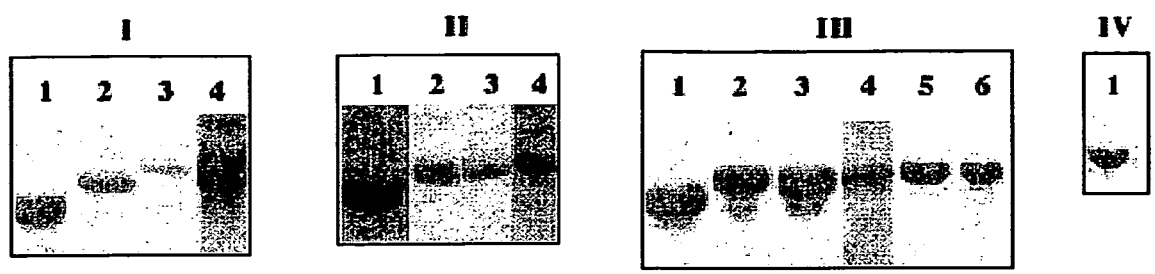
FIG. 4—Representatives of SDS-PAGE of purified carrier proteins and their CTP-containing fusion proteins. I. CagA: lane 1, native; lane 2, NGR (B); lane 3, RGD (A); lane 4, SMS (B). II. NcsA: lane 1, native; lane 2, NGR (A); lane 3, NGR (C); lane 4, RGD (A). III. BlmA: lane 1, native; lane 2, NGR (A); lane 3, NGR (B); lane 4, RGD (A); lane 5, RGD (B); lane 6, SMS (B). IV. Mrd: lane 1, native. See FIGS. 3A–D for fusion configurations denoted as FIG. 3A, FIG. 3B, FIG. 3C, or FIG. 3D.

Protein purification was done using Ni-NTA agarose (Qiagen, Santa Clarita, Calif.) according to the protocols suggested by the manufacture. The purified proteins were dialysed against 1× PBS buffer. Table 1 summarized carrier proteins and their various CTP-containing fusion proteins that have been overproduced to date. The purity of the proteins was confirmed by SDS-PAGE as exemplified in FIG. 4. Protein concentration was determined by spectroscopic method. The average yields of the recombinant proteins were about 50–100 mg/l. The identity of the fusion proteins was further verified by mass spectrometry.

solution was removed, and the cells were washed 3 times with 1 ml of 1× PBS buffer each. The culture slides were then sent for fluorescent imaging. While no significant fluorescence was detected with the native CagA, NcsA, or BlmA, the CTP-containing CagA, NcsA, and BlmA yielded intense fluorescence, indicative of CTP-targeted specific binding of the carrier proteins to the cancer cells (FIG. 6). These results clearly demonstrated the capability of CTP-containing carrier proteins to act as a targeted drug delivery system, serving as a proof-of-principle of the technology.

TABLE 1

Production and purification of carrier proteins and their CTP-containing fusion proteins

| Carrier | Native[a] | | NGR[b] | | | | RGD[b] | | | | SMS[b] | | | |
|---|---|---|---|---|---|---|---|---|---|---|---|---|---|---|
| Protein | N-His$_6$ | C-His$_8$ | A | B | C | D | A | B | C | D | A | B | C | D |
| CagA | + | − | + | + | − | − | + | + | − | − | − | + | − | − |
| NcsA | + | − | + | + | + | + | + | + | + | + | − | − | − | − |
| BlmA | + | + | + | + | + | + | + | + | + | + | + | + | − | − |
| PlmA | + | + | − | + | − | − | − | + | − | − | − | + | − | − |
| Mrd | + | + | + | − | + | − | + | − | + | − | − | − | − | − |

[a]N-His$_6$-tagged and C-His$_8$-tagged native carrier proteins were overproduced in pEF14M and pET37M, respectively (see FIG. 1).
[b]The CTP-containing carrier protein fusions were overproduced as version A, B, C, or D in the configurations as specified in FIG. 3.

Example 7

Culture Condition of Cancer Cell Lines

WM115 (high-level expression of $\alpha_v\beta_3$ integrin) and MCF7 (low level expression of $\alpha_v\beta_3$ integrin, about 10% of WM115) cell lines were grown in α MEM medium enriched with 10% fetal bovine serum (FBS) and 60 μg/ml of penicillin and 100 μg/ml of streptomycin. KS1617 cell line (high-level expression of CD13) was grown in RPMI1640 medium also enriched with 10% FBS and 60 μg/ml of penicillin and 100 μg/ml of streptomycin. The cell cultures were passed to fresh medium every 2–3 days. For fluorescent imaging, the cells were grown in 4-well culture slides to about 70% confluence before use.

Example 8

Figure 5:
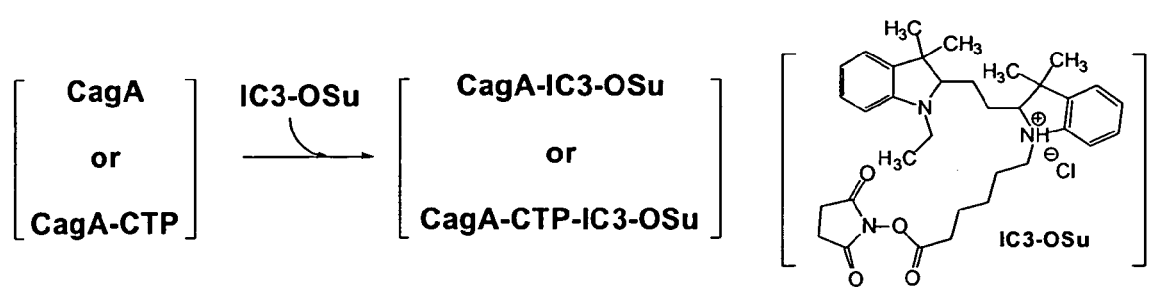
FIG. 5—Labeling of the recombinant carrier proteins with the fluorescence probe ICS-OSu as exemplified with CagA and its CTP-containing fusion proteins.

Evaluation of Binding Specificity of CTP-Containing Carrier Proteins to Cancer Cells To facilitate detection, the recombinant CTP-containing carrier proteins were labeled with Dojindo IC3-Osu, which reacts with lysine residues of the protein, according to the recommended protocols by the manufacturer (Dojindo, Gaithersburg, Md.) (FIG. 5). About 0.5 mg/ml protein was reacted with 3-fold excess of the fluorescent dye in dark at room temperature for 1 hr, and the extra dye was removed using Bio-Rad Econo-Pac desalting column. The labeling efficiency was measured using UV-vis spectroscopy. On average, about 25–35% of protein molecules were labeled.

The binding specificity between CTP-containing carrier proteins and various cancer cell lines was evaluated with both the native carrier proteins and normal cell lines as negative controls. The culture medium was first removed from the wells of the cultured cells, and the labeled protein (100 μl of a 0.1 mg/ml solution) was then added. After incubation at room temperature for about 10 min, the protein All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

X. REFERENCES

The following references, to the extent that they provide exemplary procedural or other details supplementary to those set forth herein, are specifically incorporated herein by reference.

U.S. Pat. No. 5,380,721
U.S. Pat. No. 4,659,774
U.S. Pat. No. 4,680,338
U.S. Pat. No. 4,682,195
U.S. Pat. No. 4,683,202
U.S. Pat. No. 4,684,611
U.S. Pat. No. 4,797,368
U.S. Pat. No. 4,816,571
U.S. Pat. No. 4,879,236
U.S. Pat. No. 4,952,500
U.S. Pat. No. 4,959,463
U.S. Pat. No. 5,139,941
U.S. Pat. No. 5,141,648

U.S. Pat. No. 5,141,813
U.S. Pat. No. 5,220,007
U.S. Pat. No. 5,221,605
U.S. Pat. No. 5,238,808
U.S. Pat. No. 5,264,566
U.S. Pat. No. 5,284,760
U.S. Pat. No. 5,302,523
U.S. Pat. No. 5,322,783
U.S. Pat. No. 5,354,670
U.S. Pat. No. 5,366,878
U.S. Pat. No. 5,384,253
U.S. Pat. No. 5,389,514
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,563,250
U.S. Pat. No. 5,574,146
U.S. Pat. No. 5,602,244
U.S. Pat. No. 5,610,042
U.S. Pat. No. 5,635,377
U.S. Pat. No. 5,645,897
U.S. Pat. No. 5,705,629
U.S. Pat. No. 5,789,166
U.S. Pat. No. 5,798,208
U.S. Pat. No. 5,830,650
U.S. Pat. No. 5,856,456
U.S. Pat. No. 5,871,986
U.S. Pat. No. 5,880,270
U.S. Pat. No. 5,925,565
U.S. Pat. No. 5,928,906
U.S. Pat. No. 5,935,819
U.S. Pat. No. 5,994,136
U.S. Pat. No. 6,013,516
European Appl. EP 0273085
European Appl. EP 266,032
PCT Appl. WO 94/09699
PCT Appl. WO 95/06128
PCT Appl. WO 97/26334
PCT Appl. WO 97/26321
PCT Appl. WO 84/03564
Almendro et al., *J. Immunol.*, 157(12):5411–5421, 1996.
Ando, et al., *Tetrahedron Lett.*, 39:6495, 1998.
Angel et al., *Cell*, 49:729, 1987b.
Angel et al., *Mol. Cell. Biol.*, 7:2256, 1987.
Angel et al., *Mol. Cell. Biol.*, 7:2256, 1987a.
Arap et al., *Proc. Natl. Acad. Sci. USA*, 99:1527–1531, 2002.
Arap et al., *Science*, 279:377–380, 1998.
Asai et al., *N. FEBS Lett.*, 510:206–210, 2002.
Assa-Munt et al., *Biochemistry*, 40:2373–2378, 2001.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1994.
Bae et al., *J. Biol. Chem.*, 275:13588–13596, 2000.
Baichwal and Sugden, In: *Gene Transfer*, Kucherlapati (Ed.), New York, Plenum Press, 117–148, 1986.
Banerji et al., *Cell*, 27(2 Pt 1):299–308, 1981.
Banerji et al., *Cell*, 33(3):729–740, 1983.
Barany and Merrifield, In: *The Peptides*, Gross and Meienhofer (Eds.), Academic Press, New York, 1–284, 1979.
Berkhout et al., *Cell*, 59:273–282, 1989.
Binetruy-Toumaire et al., *EMBO J.*, 19:1525–1533, 2000.
Blackburn et al., *J. Lipid. Res.*, 32(12):1911–1918, 1991.
Blanar et al., *EMBO J.*, 8:1139, 1989.
Blomer et al., *J. Virol.*, 71(9):6641–6649, 1997.
Bodine and Ley, *EMBO J.*, 6:2997, 1987.
Boothman et al., *Cancer Res.*, 49(11):2871–8, 1989.
Borek, *Carcinog. Compr. Surv.*, 10:303–316, 1985.
Boshart et al., *Cell*, 41:521, 1985.
Bosze et al, *EMBO J.*, 5(7):1615–1623, 1986.
Braddock et al., *Cell*, 58:269, 1989.
Braisted and Wells, *Proc. Natl. Acad. Sci. USA*, 93(12): 5688–5692, 1996.
Brukner, *Curr. Opin. Oncol. Endocr. Met. Invest. Drugs*, 2:344, 2000.
Buhl et al., *Br. J. Haematol.*, 116:549–554, 2002.
Bulla and Siddiqui, *J. Virol.*, 62:1437, 1986.
Burg et al., *Cancer Res.*, 59:2869–2874, 1999.
Burks et al., *Proc. Natl. Acad. Sci. USA*, 94(2):412–417, 1997.
Burton and Barbas, *Adv. Immunol.*, 57:191–280, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Cane et al., *Science*, 6:319, 1998.
Carbonelli et al., *FEMS Microbiol. Lett.*, 177(1):75–82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596–601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.*, 7(8):2745–2752, 1987.
Choi et al., *Cell*, 53:519, 1988.
Christou et al., *Proc. Natl. Acad. Sci. USA*, 84(12):3962–3966, 1987.
Cocea, *Biotechniques*, 23(5):814–816, 1997.
Cohen et al., *J. Cell. Physiol.*, 5:75, 1987.
Cooley et al., *Science*, 239(4844):1121–1128, 1988.
Costa et al., *Mol. Cell. Biol.*, 8:81, 1988.
Cotton et al., *Proc. Natl. Acad. Sci. USA*, 89(13):6094–6098, 1992.
Coupar et al., *Gene*, 68:1–10, 1988.
Cripe et al, *EMBO J.*, 6:3745, 1987.
Culotta and Hamer, *Mol. Cell. Biol.*, 9:1376, 1989.
Cunningham and Wells, *Science*, 244(4908):1081–1085, 1989.
Curiel, *Nat. Immun.*, 13(2–3):141–64, 1994.
Dandolo et al., *J. Virology*, 47:55–64, 1983.
De Villiers et al., *Nature*, 312(5991):242–246, 1984.
Dedon and Goldberg, *Chem. Res. Toxicol.*, 5:311, 1992.
Deschamps et al., *Science*, 230:1174–1177, 1985.
D'Halluin et al., *Plant Cell*, 4(12):1495–1505, 1992.
Doyle and Border, In: *Enediyne Entibiotics as Antitumor Agents*, Marcel-Dekker: NY, 1995.
Du and Shen, *Curr. Opinion Drug Discov. Dev.*, 4:215, 2001.
Dziegielewski and Beerman, *J. Biol. Chem.*, 277:20549, 2002.
Edbrooke et al., *Mol. Cell. Biol.*, 9:1908, 1989.
Edlund et al., *Science*, 230:912–916, 1985.
Edo et al., *Tetrahedron Lett.*, 26:331, 1985.
Essler and Ruoslahti, *Proc. Natl. Acad. Sci. USA*, 99:2252–2257, 2002.
Fechheimer et al., *Proc. Natl. Acad. Sci. USA*, 84:8463–8467, 1987.
Feng and Holland, *Nature*, 334:6178, 1988.
Firak and Subramanian, *Mol. Cell. Biol.*, 6:3667, 1986.
Foecking and Hofstetter, *Gene*, 45(1):101–105, 1986.

Fraley et al., *Proc. Natl. Acad. Sci. USA*, 76:3348–3352, 1979.
Friedmann, *Science*, 244:1275–1281, 1989.
Froehler et al., *Nucleic Acids Res.*, 14(13):5399–5407, 1986.
Fujita et al., *Cell*, 49:357, 1987.
Fukuda et al., *Cancer Res.*, 60:450–456, 2000.
Gilles et al., *Cell*, 33:717, 1983.
Gloss et al., *EMBO J.*, 6:3735, 1987.
Godbout et al., *Mol. Cell. Biol.*, 8:1169, 1988.
Golik et al., *Am. Chem. Soc.*, 109:3461, 1987a.
Golik et al., *Am. Chem. Soc.*, 109:3462, 1987b.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188–1190, 1985.
Graham and Van Der Eb, *Virology*, 52:456–467, 1973.
Greene et al., *Immunology Today*, 10:272, 1989
Grosschedl and Baltimore, *Cell*, 41:885, 1985.
Grunhaus et al., *Seminar in Virology*, 200(2):535–546, 1992.
Harland and Weintraub, *J. Cell Biol.*, 101:1094–1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hensens et al., *Proc. Natl. Acad. Sci. USA*, 91A:4534, 1994.
Herr and Clarke, *Cell*, 45:461, 1986.
Hilton et al., *J. Biol. Chem.*, 271(9):4699–4708, 1996.
Hirochika et al., *J. Virol.*, 61:2599, 1987.
Hirsch et al., *Mol. Cell. Biol.*, 10:1959, 1990.
Ho et al., *Proc. Natl. Acad. Sci. USA*, 91:9203, 1994.
Holbrook et al., *Virology*, 157:211, 1987.
Hong and Clayman, *Cancer Res.*, 60:6551–6556, 2000.
Hopwood, *Chem. Rev.*, 97:2465, 1997.
Horlick and Benfield, *Mol. Cell. Biol.*, 9:2396, 1989.
Horwich et al., *J. Virol.*, 64:642–650, 1990.
Hou and Lin, *Plant Physiology*, 111: 166, 1996.
Huang et al., *Cell*, 27:245, 1981.
Hug et al., *Mol. Cell. Biol.*, 8:3065, 1988.
Hwang et al., *Mol. Cell. Biol.*, 10:585, 1990.
Iida et al., *Tetrahedron Lett.*, 37:4997, 1996.
Ikemoton et al., *Proc. Natl. Acad. Sci. USA*, 92:10506, 1995.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Inouye and Inouye, *Nucleic Acids Res.*, 13: 3101–3109, 1985.
Ishida et al., *J. Antibiot.*, 18:68, 1965.
Ivanenko et al., *Biochim. Biophys. Acta*, 1449:463–472, 1999.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Fouad, *Curr. Pharm. Des.*, 8:2415, 2002.
Kadesch and Berg, *Mol. Cell. Biol.*, 6:2593, 1986.
Kaeppler et al., *Plant Cell Reports*, 9:415–418, 1990.
Kaneda et al., *Science*, 243:375–378, 1989.
Kappen and Goldberg, *Science*, 261:1319, 1993.
Karin et al., *Mol. Cell. Biol.*, 7:606, 1987.
Karin et al., *Mol. Cell. Biol.*, 7:606, 1987.
Katinka et al., *Cell*, 20:393, 1980.
Kato et al., *J. Biol. Chem.*, 26.6:3361–3364, 1991.
Kawamoto et al., *Mol. Cell. Biol.*, 8:267, 1988.
Kelleher and Vos, *Biotechniques*, 17(6):1110–7, 1994.
Kennel et al., *Nucl. Med. Biol.*, 27:815–825, 2000.
Kieser et al., In: *Practical Streptomyces Genetics*, The John Innes Foundation, Norwich, UK, 2000.
Kiledjian et al., *Mol. Cell. Biol.*, 8:145, 1988.
Klamut et al., *Mol. Cell. Biol.*, 10:193, 1990.
Klein et al., *Nature*, 327:70–73, 1987.
Koch et al., *Mol. Cell. Biol.*, 9:303, 1989.
Koivunen et al., *BioTechnology*, 13:265, 1995.
Koivunen et al., *Nature Biotechnol.*, 17:768–774, 1999.
Koncz et al., *EMBO J.*, 9(5):1337–1346, 1990.
Konishi et al., *J. Antibiot.*, 42:1449, 1989.
Kraus et al., *FEBS Lett.*, 428(3):165–170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Lambert and Borek, *J. Natl. Cancer Inst.*, 80(18):1492–1497, 1988.
Lareyre et al., *J. Biol. Chem.*, 274(12):8282–8290, 1999.
Larsen et al., *Proc. Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515–524, 1986.
Lebkowski et al., *Mol. Cell. Biol.*, 8(10):3988–3996, 1988.
Lee et al., *Am. Chem. Soc.*, 109:3464, 1987a.
Lee et al., *Biochem. Biophys. Res. Commun.*, 240(2):309–313, 1997.
Lee et al., *Environ. Mol. Mutagen.*, 13(1):54–59, 1989.
Lee et al., *J. Am. Chem. Soc.*, 109:3466, 1987b.
Lee et al., *Nature*, 294:228, 1981.
Lee et al., *Nucleic Acids Res.*, 12:4191–206, 1984.
Leet et al., *J. Am. Chem., Soc.*, 114:7946, 1992.
Levenson et al., *Hum. Gene Ther.*, 9(8):1233–1236, 1998.
Levinson et al., *Nature*, 295:79, 1982.
Lin et al., *Mol. Cell. Biol.*, 10:850, 1990.
Luria et al, *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90–94, 1991.
Maeda et al., In: *Neocarzinostatin: The Past, Present, and Future of an Anticancer Drug*, Springer-Verlag: NY, 1997.
Majors and Varmus, *Proc. Natl. Acad. Sci. USA*, 80:5866, 1983.
Maniatis, et al., Molecular Cloning, A Laboratory Manual, Cold Spring Harbor Press, Cold Spring Harbor, N.Y., 1988.
Mann et al., *Cell*, 33:153–159, 1983.
Marks et al., *J. Mol. Biol.*, 222:581–597, 1991.
Martin et al., *Structure*, 10:933–942, 2002.
McCann et al., *Proc. Natl. Acad. Sci. USA*, 72(3):979–983, 1975.
McDonald et al., *J. Am. Chem. Soc.*, 118:10898, 1996.
McLaughlin et al., *J. Virol.*, 62(6):1963–1973, 1988.
McNeall et al., *Gene*, 76:81, 1989.
Merrifield, *Science*, 232:341–347, 1986.
Miksicek et al., *Cell*, 46:203, 1986.
Miller et al., *Am. J. Clin. Oncol.*, 15(3):216–221, 1992.
Minami et al., *Tetrahedron Lett.*, 34:2633, 1993.
Mordacq and Linzer, *Genes and Dev.*, 3:760, 1989.
Moreau et al., *Nucl. Acids Res.*, 9:6047, 1981.
Muesing et al., *Cell*, 48:691, 1987.

Muzyczka, *Curr. Topics Microbiol. Immunol.*, 158:97–129, 1992.
Myers et al., *Chem. Biol.*, 2:33, 1995.
Nabel et al., *Science*, 244(4910):1342–1344, 1989.
Naldini et al., *Science*, 272(5259):263–267, 1996.
Ng et al., *Nuc. Acids Res.*, 17:601, 1989.
Nicolaou et al., *Chem. Int. Ed. Engl.*, 30:1387, 1991.
Nicolaou et al., *Proc. Natl. Acad. Sci. USA*, 90:3142, 1993.
Nicolas and Rubinstein, In: *Vectors: A survey of molecular cloning vectors and their uses*, Rodriguez and Denhardt (Eds.), Stoneham: Butterworth, 494–513, 1988.
Nicolau and Sene, *Biochim. Biophys. Acta*, 721:185–190, 1982.
Nicolau et al., *Methods Enzymol.*, 149:157–176, 1987.
Nomoto et al., *Gene*, 236(2):259–271, 1999.
Oku et al., *J. Am. Chem. Soc.*, 125:2044, 2003.
Omirulleh et al., *Plant Mol. Biol.*, 21(3):415–28, 1993.
Ondek et al., *EMBO J.*, 6:1017, 1987.
Oppenheimer et al., *Cell*, 67(3):483–493, 1991.
Ornitz et al., *Mol. Cell. Biol.*, 7:3466, 1987.
Otani et al., *J. Antibiot.*, 52:415, 1999.
Palmiter et al., *Nature*, 300:611, 1982.
Paskind et al., *Virology*, 67:242–248, 1975.
Pasqualini et al., *Cancer Res.*, 60:722–727, 2000.
Pech et al., *Mol. Cell. Biol.*, 9:396, 1989.
Pelletier and Sonenberg, *Nature*, 334:320–325, 1988.
Perales et al., *Proc. Natl. Acad. Sci. USA*, 91:4086–4090, 1994.
Perez-Stable and Constantini, *Mol. Cell. Biol.*, 10:1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183–188, 1985.
Potter et al., *Proc. Natl. Acad. Sci. USA*, 81:7161–7165, 1984.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Remington's Pharmaceutical Sciences, 15th ed., pages 1035–1038 and 1570–1580, Mack Publishing Company, Easton, Pa., 1980.
Renschler et al., *Proc. Natl. Acad. Sci. USA*, 91:3623, 1994.
Resendez Jr. et al., *Mol. Cell. Biol.*, 8:4579, 1988.
Rhodes et al., *Methods Mol. Biol.*, 55:121–131, 1995.
Ridgeway, In: *Vectors: A survey of molecular cloning vectors and their uses*, Rodriguez and Denhardt (Eds.), Stoneham: Butterworth, 467–492, 1988.
Ripe et al., *Mol. Cell. Biol.*, 9:2224, 1989.
Rippe et al., *Mol. Cell Biol.*, 10:689–695, 1990.
Rittling et al., *Nuc. Acids Res.*, 17:1619, 1989.
Rodriguez and McDaniel, *Curr. Opinion Microbiol.*, 4:526, 2001.
Romanov et al., *Prostate*, 47:239–251, 2001.
Rosen et al., *Cell*, 41:813, 1988.
Roux et al., *Proc. Natl. Acad. Sci. USA*, 86:9079–9083, 1989.
Sakai et al., *Genes and Dev.*, 2:1144, 1988.
Sambrook et al., Cold Spring Harbor Laboratory, old Spring Harbor, N.Y., 1989.
Satake et al., *J. Virology*, 62:970, 1988.
Schaffner et al., *J. Mol. Biol.*, 201:81, 1988.
Schmidt et al., *Science*, 238(4829):960–963, 1987.
Schor et al., *Brain Res.*, 831:125, 1999.
Schroeder et al., *J. Am. Chem. Soc.*, 116:9351, 1994.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Shen, *Curr. Top. Chem.*, 209:1, 2000.
Sherman et al., *Mol. Cell. Biol.*, 9:50, 1989.
Sielvers et al., *Blood*, 93:3678, 1999.
Sleigh and Lockett, *J. EMBO*, 4:3831, 1985.
Smith and Nicolaou, *J. Med. Chem.*, 39:2103, 1996.
Smith and Rutledge, *Natl. Cancer Inst. Monogr.*, 42:141–143, 1975.
Sommer et al., *EMBO J.*, 9(3):605–613, 1990.
Spalholz et al., *Cell*, 42:183, 1985.
Spandau and Lee, *J. Virology*, 62:427, 1988.
Spandidos and Wilkie, *EMBO J.*, 2:1193, 1983.
Stassinopoulos et al., *Science*, 272:1943, 1996.
Staunton and Wessman, *Nat. Prod. Rep.*, 18:380, 2001.
Stephens and Hentschel, *Biochem. J.*, 248:1, 1987.
Stewart and Young, Solid Phase Peptide Synthesis, 2d. ed., Pierce Chemical Co., 1984.
Strohl, *Met. Engineer*, 3:4, 2001.
Stuart et al., *Nature*, 317:828, 1985.
Sugiura et al., *Proc. Natl. Acad. Sci. USA*, 87:3831, 1990.
Sugiyama et al., *J. Biol. Chem.*, 277(3):2311–2320, 2002.
Sullivan and Peterlin, *Mol. Cell. Biol.*, 7:3315, 1987.
Swartzendruber and Lehman, *J. Cell. Physiology*, 85:179, 1975.
Szecsi et al., *Br. J. Haematol.*, 107:357–364, 1999.
Takebe et al., *Mol. Cell. Biol.*, 8:466, 1988.
Tam et al., *J. Am. Chem. Soc.*, 105:6442, 1983.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149–188, 1986.
Thiesen et al., *J. Virology*, 62:614, 1988.
Thrson et al., *Curr. Pharm. Des.*, 6:1841, 2000.
Tratschin et al., *Mol. Cell. Biol.*, 4:2072–2081, 1984.
Treisman, *Cell*, 42:889, 1985.
Tronche et al., *Mol. Biol. Med.*, 7:173, 1990.
Trudel and Constantini, *Genes and Dev.* 6:954, 1987.
Tsumaki et al., *J. Biol. Chem.*, 273(36):22861–22864, 1998.
Tur-Kaspa et al., *Mol. Cell Biol.*, 6:716–718, 1986.
Tyndell et al., *Nuc. Acids. Res.*, 9:6231, 1981.
Van Wezel, *Nature*, 216(110):64–65, 1967.
Vannice and Levinson, *J. Virology*, 62:1305, 1988.
Vasseur et al., *Proc. Natl. Acad. Sci. U.S.A.*, 77:1068, 1980.
Wagner et al., *Proc. Natl. Acad. Sci. USA* 87(9):3410–3414, 1990.
Walsh, *ChemBioChem.*, 3:124, 2002.
Wang and Calame, *Cell*, 47:241, 1986.
Warren et al., *Biochemistry*, 35(27):8855–8862, 1996.
Wawrzynczak and Thorpe, *FEBS Lett.*, 207(2):213–216, 1986.
Weber et al., *Cell*, 36:983, 1984.
Weinberger et al., *Mol. Cell. Biol.*, 8:988, 1984.
Wells et al., *J. Leukoc. Biol.*, 59(1):53–60, 1996.
Wilson et al., *Science*, 244:1344–1346, 1989.
Winoto and Baltimore, *Cell* 59:649, 1989.
Witte et al., *Cancer Res.*, 49(18):5066–72, 1989.
Wong et al., *Gene*, 10:87–94, 1980.
Wu and Wu, *Adv. Drug Delivery Rev.*, 12:159–167, 1993.
Wu and Wu, *Biochemistry*, 27:887–892, 1988.
Wu and Wu, *J. Biol. Chem.*, 262:4429–4432, 1987.
Wu et al., *Biochem. Biophys. Res. Commun.*, 233(1):221–6, 1997.

Wu et al., *Eur. J. Biochem.*, 267:6212, 2000.
Xi and Goldberg, In: *Comprehensive Natural Products Chemistry*, Barton et al. (Eds.), Elseiver: NY, 7:553, 1999.
Yang et al., *Proc. Natl. Acad. Sci. USA*, 87:9568–9572, 1990.
Yelton et al., *J. Immunol.*, 155(4):1994–2004, 1995.
Yoshida et al., *Tetrahedron Lett.*, 34:2637, 1993.
Young et al., *N. Engl. J. Med.*, 7:299(23):1261–1266, 1978.
Yu et al., *J. Biol. Chem.*, 269:4144, 1994.
Yutzey et al., *Mol. Cell. Biol.*, 9:1397, 1989.
Zein et al., *Proc. Natl. Acad. Sci. USA*, 90:2822, 1993.
Zeng et al., *Biochemistry*, 35(40):13157–13164, 1996.
Zhang et al., *Cancer Lett.*, 171:153–164, 2001.
Zhao-Emonet et al., *Biochim. Biophys. Acta*, 1442(2–3):109–119, 1998.
Zhou et al., *Exp. Hematol.*, 21:928–933, 1993.
Zufferey et al., *Nat. Biotechnol.*, 15:871–875, 1997.

What is claimed is:

1. A fusion protein comprising a drug-binding portion of a naturally-occurring carrier polypeptide and a cancer cell- or tumor vasculature-targeting peptide, wherein said carrier polypeptide is an apoprotein or a binding protein.

2. The fusion protein of claim 1, wherein said apoprotein is CagA or NscA.

3. The fusion protein of claim 1, wherein said binding protein is a biosynthetic gene cluster protein or a pathogen drug-resistance protein.

4. The fusion protein of claim 3, wherein said biosynthetic gene cluster protein is BlmA, PlmA or MRD.

5. The fusion protein of claim 1, wherein said cancer cell is a pancreatic cancer cell, a liver cancer cell, a lymphoma cell, a myeloma cell, a neuroblastoma cell, a breast cancer cell, a prostate cancer, or a head and neck cancer cell.

6. The fusion protein of claim 1, further comprising a drug complexed with said fusion protein.

7. The fusion protein of claim 6, wherein said drug is selected from the group consisting of an antibiotic, a plant akyloid, an alkylating agent, a DNA repair inhibitor or a DNA cleaving agent.

8. The fusion protein of claim 6, wherein said DNA cleaving agent is an enediyne.

9. The fusion protein of claim 1, wherein said first cell-targeting peptide is attached at the N-terminus of said carrier polypeptide.

10. The fusion protein of claim 1, wherein said first cell-targeting peptide is attached at the C-terminus of said carrier polypeptide.

11. The fusion protein of claim 1, wherein said first cell-targeting peptide is inserted as a continuous segment into said carrier polypeptide.

12. The fusion protein of claim 1, wherein said fusion protein comprises multiple copies of said cell-targeting peptide.

13. The fusion protein of claim 1, further comprising a second cell-targeting peptide.

14. The fusion protein of claim 1, wherein said tumor vasculature-targeting peptide is derived from pancreatic cancer, liver cancer, lymphoma, myeloma, neuroblastoma, breast cancer, prostate cancer or head and neck cancer.

* * * * *

UNITED STATES PATENT AND TRADEMARK OFFICE
CERTIFICATE OF CORRECTION

| | |
|---|---|
| PATENT NO. | : 7,122,353 B2 |
| APPLICATION NO. | : 10/912764 |
| DATED | : October 17, 2006 |
| INVENTOR(S) | : Ben Shen |

Page 1 of 1

It is certified that error appears in the above-identified patent and that said Letters Patent is hereby corrected as shown below:

Title page, item [57], line 2, delete "drug carries" and insert --drug carriers-- therefor.

Signed and Sealed this

Twenty-fourth Day of April, 2007

JON W. DUDAS
*Director of the United States Patent and Trademark Office*